United States Patent [19]
Gulbenk et al.

[11] 3,956,338
[45] May 11, 1976

[54] 4,6-DIBROMO-5-HYDROXY-2-PYRIDINE NITRILE COMPOUNDS AND METHOD OF PREPARATION

[75] Inventors: Alin H. Gulbenk; Sven H. Ruetman, both of Walnut Creek, Calif.

[73] Assignee: The Dow Chemical Company, Midland, Mich.

[22] Filed: Jan. 17, 1975

[21] Appl. No.: 541,811

[52] U.S. Cl.............. 260/294.9; 260/247.2 R; 260/247.5 G; 260/293.69; 260/270 PY; 71/94; 424/248; 424/263; 424/267
[51] Int. Cl.² ...................................... C07D 213/57
[58] Field of Search............... 260/294.9, 270 PY

[56] References Cited
OTHER PUBLICATIONS
Klingsberg, "Pyridine and Its Derivatives," Part Three, Interscience, p. 219, (1962).
Teague et al., Organic Synthesis, Vol. 33, pp. 52–53, John Wiley & Sons Pub. (1953).

*Primary Examiner*—Alan L. Rotman
*Attorney, Agent, or Firm*—Robert R. Stringham

[57] ABSTRACT

The invention is a genus of compounds of the formula

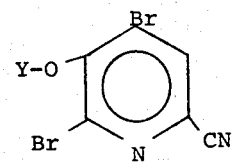

wherein Y is H, M or RCO—; R is a primary or secondary $C_1$–$C_{12}$ alkyl group, a $C_5$–$C_7$ cycloalkyl group, phenyl or a $C_7$–$C_{12}$ phenalkyl or alkylphenyl group and M is a metal or ammonium cation. The compounds have utility as intermediates and as herbicides.

3 Claims, No Drawings

4,6-DIBROMO-5-HYDROXY-2-PYRIDINE NITRILE COMPOUNDS AND METHOD OF PREPARATION

REFERENCE TO RELATED APPLICATION

Application Ser. No. 546,812, attorneys docket number C-17,555, co-filed herewith and entitled "Selectively Herbicidal 4,6-Dibromo-5-Hydroxy-2-Pyridine Carboxamide, Salts and Esters Thereof and Methods of Preparation and Use", is incorporated herein by reference.

BACKGROUND OF THE INVENTION

The compounds of the present application are intermediates for the preparation of the compounds of the companion application above referred to.

The compound, 3,5-dibromo-4-hydroxy benzonitrile, is a commercial herbicide (BROMINIL). K. Carpenter et al. have reported (Mededel Landbouwhogeschool Opzoekingsta. Start Gent 29(3), 644–54 (1964; in English)) that the number of halogen substituents and the positions of both the halogen and hydroxy substituents is critical to the activity level of this compound. Conversion of the —CN group to a —CONH$_2$ group was found detrimental to activity. U.S. Pat. No. 3,317,549 discloses 3,6-dichloro-2-pyridine-carboxylic acid-derived herbicides, including the nitrile. No hydroxy groups are present on the pyridine ring.

Belgian Pat. No. 698,384 discloses, as intermediates, compounds of the formula

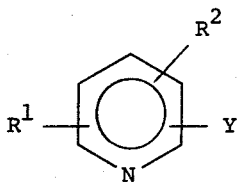

where $R^1$ and $R^2$ independently may be halogen or cyano, among other moieties and Y may be hydroxyl, among other moieties. The end products prepared from these compounds are binuclear compounds and the only utilities disclosed for them are as antiphlogistics and analgesics.

SUMMARY DESCRIPTION OF THE INVENTION

The invention is a genus of compounds of the formula

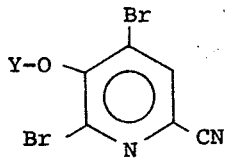

wherein Y is H, M or R—CO—; R is a primary or secondary $C_1$–$C_{12}$ alkyl group, a $C_5$–$C_7$ cycloalkyl group, phenyl or a $C_7$–$C_{12}$ phenalkyl or alkylphenyl group and M is a cation of lithium, sodium, potassium, calcium, magnesium, barium, aluminum, a metal of atomic number 24 through 30 or tin; or M is an ammonium ion $(H—NR'R_2'')^+$, R' being H, an alkyl or alkenyl group of 1 to 22 carbons, a cycloalkyl group of 3 to 7 carbons, a hydroxy-alkyl group of 2–4 carbons or benzyl; and the two R'' groups, together with the nitrogen, constitute a morpholine or piperdine ring or are independently defined as is R'.

The compounds of the preceding genus are not only useful as intermediates for preparation of the corresponding amides, for they also have herbicidal, fungicidal and insecticidal activity in their own right. Further they are intermediates for the preparation of 4,6-dibromo-5-hydroxy-2-pyridine carboxylic acid, which has utility as a monomer or cross-linker in the preparation of fire retardant polyesters, epoxides, polyurethanes, etc.

Among the preceding compounds, those in which Y is H, Na$^+$, acetyl or $—(H—N—R'R_2'')^+$ — as above defined — are preferred as being more active herbicides. The amine salts derived from triethanolamine and N-methyl morpholine are the most preferred species in which Y is $(H—NR'R_2'')^+$.

The compounds of the invention are white to off-white solids. 4,6-Dibromo-5-hydroxy-2-pyridine nitrile is essentially insoluble in water and is soluble in the common organic solvents. The compounds of the invention which are salts are soluble in water and generally of low solubility in the common organic solvents.

In a process embodiment, the invention is the method of preparing 4,6-dibromo-5-hydroxy-2-pyridine nitrile which comprises dehydrating the amide group in 4,6-dibromo-5-hydroxy-2-pyridine carboxamide by reaction of the latter compound with phosphorous pentoxide in an inert liquid medium. The preferred medium is tetrachloroethane.

A method of preparing the carboxamide precursor is disclosed in the companion application referred to earlier herein.

DETAILED DESCRIPTION OF THE INVENTION

The most preferred compound of the preceding genus is 4,6-dibromo-5-hydroxy-2-pyridine nitrile itself. This compound, in post-emergent application, controlled wild oats at a concentration of 500 parts per million. By comparison, control was not obtained at 4000 ppm with 3,5-dibromo-4-hydroxybenzonitrile under identical conditions.

HOW THE COMPOUNDS ARE MADE 4,6-Dibromo-5-hydroxy-2-pyridine nitrile is prepared, in a preferred version of the present process invention, as follows.

4,6-Dibromo-5-hydroxy-2-pydridine carboxamide is dispersed, i.e., suspended, dissolved or slurried in an inert liquid medium. The dispersion is heated and stirred with at least an equivalent amount of phosphorous pentoxide (1/6 mole of $P_4O_{10}$ per mole of the amide) for at least 1 hour at a temperature of from about 50° up to the boiling point of the medium. The reaction mixture is worked up by any suitable combination of conventional procedures, such as filtration (to remove any solid starting materials or by-products) washing the filtrate with ice water (to remove dissolved inorganic phosphorous compounds), drying, stripping and recrystallization, for example.

Preferably, the precursor amide suspension is contacted with at least one molecular proportion of phosphorous pentoxide per molecular proportion amide for at least 2 hours at a temperature of from about 100° to about 150°C.

The term "inert liquid medium" is used herein to denote an otherwise suitable liquid which does not detrimentally react, to an intolerable degree, with any of the material present in the reaction mixture. Examples of such liquids are halocarbons, such as tetrachloroethanes, perchloroethylene and allomers of tetrafluoro ethylene; and hydrocarbons, such as octadecane, xylene or dimethano naphthalene.

Pressure is not a critical variable in the process of the present invention, except that a pressure at least equal to the autogenous pressure will be required when employing volatile solvents, such as perchloroethylene, for example. Subatmospheric pressures may be employed but atmospheric pressure is most convenient.

The compounds of the present invention in which Y is other than H are made from 4,6-dibromo-5-hydroxy-2-pyridine nitrile by conventional salt formation or esterification procedures. Metal or amine salts are made simply by contacting the dibromo cyanopyridinol in a suitable solvent or suspension medium with a suitable base, such as the metal hydroxide, ammonia or the amine. In some instances, salts of metals ($m$) which give insoluble, colloidal or only weakly basic hydroxides (hydrous oxides) are prepared by means of cation exchange between a readily prepared pyridinol salt, such as the sodium salt, and a cation exchange resin which has been contacted with a soluble salt of the metal ($m$).

The compounds in which Y is an acyl group are prepared by reacting a corresponding acyl halide with the pyridinol in the presence of a suitable hydrogen halide acceptor, such as pyridine. Alternatively, an anhydride of the corresponding carboxylic acid may be employed as an acylating agent.

HOW THE COMPOUNDS ARE USED

The compounds of the present invention are most effectively employed as post-emergent herbicides. In general, they are formulated and applied in accordance with conventional agronomic practices. 4,6-Dibromo-5-hydroxy-2-pyridine nitrile also is active against at least one microorganism and against at least one insect species and may be employed in accordance with conventional methods for formulating and applying fungicides and insecticides.

The practice of the present invention can in some instances be carried out with unmodified compounds; however, for good results, it is generally necessary that the compound be employed in modified form, that is, as one component of a composition formulated to implement the plant growth inhibiting effects. Thus, for example, the active agent can be mixed with water or other liquid or liquids, preferably aided by the usage of a surface active agent. The active agent can also be incorporated on a finely divided solid, which can be a surface active substance, to yield a wettable powder, which can subsequently be dispersed in water or other liquid, or incorporated as part of a dust which can be applied directly. Other methods of formulations are known in the art and can be employed in implementing the present invention.

The exact amount of the active agent employed is not critical and will vary, depending upon the type of growth-inhibiting effect desired, the identity of the plants concerned, the particular active agent used, weather conditions, and the like. In general, a broad growth-inhibiting effect is obtained with rates of from 3–5 to 20 pounds or more of active agent per acre, and such rates are suitable and effective for control of vegetative growth on fallow land. When it is desired to obtain a selective growth-inhibiting effect on weeds in areas planted to crabs, rates of from about 1 to 5 pounds per acre generally give good results. When in the typical mode of operation, the active agent is employed as a composition comprising the agent, the exact concentration of active agent in the composition is not critical, except that the concentration and total amount of formulation employed be adequate to supply the appropriate amount of active agent on a per acre basis. In general, good results are obtained when employing formulations containing the active agent in a concentration of from 1.0 to 5.0 percent or higher, in the instance of a dust, powder, granule, or the like. More concentrated formulations can be prepared and are often preferred in that they can serve, depending upon the particular application contemplated and the particular concentration, both as a concentrated formulation for purposes of shipment, storage, and the like, and as an ultimate treating composition. Thus, for example, formulations often preferably contain a surface active agent and the present active agent, the latter being present in an amount of from 0.5 to 99.5 percent, by weight; or an inert, finely divided solid and the present active agent, the latter being present in an amount of from 1.0 to 99.0 percent, by weight. Such formulations, as indicated, can be employed directly in certain applications, but can also be diluted and subsequently employed in many other applications.

Liquid compositions containing the desired amount of active agent are prepared by dissolving the substance in a liquid with or without the aid of a surface active dispersing agent such as an ionic or non-ionic emulsifying agent. Most preferably, the subject compound is dispersed in water or dissolved in an organic liquid carrier, aided by the use of a surface active dispersing agent. Suitable organic liquid carriers include agricultural spray oils and the petroleum distillates such as diesel fuel, kerosene, fuel oil naphthas and Stoddard solvent. The choice of dispersing and emulsifying agent and the amount thereof employed is dictated by the nature of the composition and by the ability of the agent to facilitate the dispersion of the active agent in the carrier to produce the desired composition. Dispersing and emulsifying agents which can be employed in the compositions include the condensation products of alkylene oxides with phenols and organic acids, alkyl aryl sulfonates, polyoxyalkylene derivatives or sorbitan esters, complex ether alcohols, and the like. Representative surface active agents which are suitably employed in implementing the present invention are identified in U.S. Pat. Nos. 3,095,299, second column, lines 25–36; 2,655,447, column 5, and 2,412,510, columns 4 and 5.

In the preparation of dust compositions, the active ingredient is intimately dispersed in and on a finely divided solid such as clay, talc, chalk, gypsum, limestone, vermiculite fines, perlite, and the like. In one method of achieving such dispersion, the finely divided carrier is mechanically mixed or ground with the active agent.

Similarly, dust compositions containing the toxicant compounds can be prepared with various of the solid surface active dispersing agents such as bentonite, fuller's earth, attapulgite and other clays. Depending upon the proportions of ingredients, these dust compositions can be employed as concentrates and subsequently diluted with additional solid surface active dispersing agents or with chalk, talc, or gypsum and the like to obtain the desired amount of active ingredient in a composition adapted to be employed for the suppression of the growth of the plants. Also, such dust compositions can be dispersed in water, with or without the aid of a dispersing agent, to form spray mixtures.

Formulations containing the present active agent are often advantageously further modified by incorporation therein of an effective amount of a surfactant which facilitates the dispersion and spreading of the formulation of the plant leaf surfaces and the incorporation of the formulation by the plant.

In accordance with the present invention, the active agent can be dispersed in soil or other growth media in any convenient fashion. Applications can be carried out by simply mixing with the media, by applying to the surface of soil and thereafter dragging or discing into the soil to the desired depth, or by employing a liquid carrier to accomplish the penetration and impregnation. The application of spray and dust compositions to the surface of soil, or to plant parts or the above ground surfaces of plants can be carried out by conventional methods, e.g., powder dusters, boom and hand sprayers and spray dusters, whether surface or air-borne. However, while such conventional modes of application can be used, they are not required. As above noted, it is an advantage of the present invention that the compounds serving as active agent are active and effective as herbicides when merely placed on the surface of the soil, without any additional step to assist incorporation. Thus, the compounds are of substantially the same efficacy regardless of whether they are applied to the surface only, or whether they are applied to the surface and subsequently disced into the soil.

In a further method, the distribution of the active agent in soil can be accomplished by introducing the agent with the water employed to irrigate the soil. In such procedures, the amount of water is varied with the porosity and water holding capacity of the soil to obtain a desired depth of distribution of the agent.

In addition, the present method also comprehends the employment of an aerosol composition containing one or more of the present active agents as an active compound. Such a composition is prepared according to conventional methods wherein the agent is dispersed in a solvent, and the resultant dispersion mixed with a propellant in liquid state. Such variables as the particular agent to be used and the nature of the vegetation which is to be treated will determine the desirability of the solvent and concentration of the agent therein.

Satisfactory results are obtained when the active agent of the present invention, or a composition comprising such active agent, is combined with other agricultural materials intended to be applied to plants, plant parts, or their habitats. Such materials include fertilizers fungicides, nematocides, insecticides, other herbicides, soil conditioning agents, and the like.

EXAMPLE 1

Perparations of 4,6-dibromo-5-hydroxy-2-pyridine nitrile

A. To a solution of 6.2 g. 4,6-dibromo-5-hydroxy-2-pyridine carboxamide in 25 ml. anhydrous DMF was added 2.4 g. thionyl chloride at 60°C. At the end of 2 hours, 2 ml. more thionly chloride was added and the temperature was raised to 70°C. for another hour to insure complete reaction. The product was isolated by removing the DMF under reduced pressure and triturating the residue with ice water in 73% yield; m.p. 139°–147°C. Elemental, mass spectrometric and gas liquid chromatographic analysis indicated that the product was a mixture of 4,6-dibromo-5-hydroxy-6-pyridine carbonitrile and X-bromo-X-chloro-5-hydroxy-6-pyridine carbonitrile, the major component being the latter.

B. 7 g. (0.0237 mole) of 5-hydroxy-4,6-dibromopicolinamide was slurried in 1.0 ml. of tetrachloroethane. The well stirred slurry was heated to 55°C. and 2.5 g. of phosphorous pentoxide was added. The heating was continued and two additional 2.5 g. portions of $P_2O_5$ were added at 80°C. and at 120°C. The slurry was heated under reflux (~140°C.) for 1 hour. After 30 minutes of reflux another 1.5 g. of phosphorous pentoxide was added. The slurry was filtered hot and the solid residue was extracted with ~25 ml. of hot tetrachloroethane. As the filtrate cooled, a white precipitate appeared. It was filtered (1.3 g.) and found to be unchanged starting material (IR scan). The filtrate was evaporated to dryness, leaving a 4 gram solid residue. IR scan identified it as 5-hydroxy-4,6-dibromopicolinonitrile (strong —CN absorption at 4.495μ). The yield was 74.7%. The solid was recrystalized once from benzene/hexane mixture and once from methanol/water mixture to give an analytically pure sample; m.p. 179°–80°C.

Found: C = 26.0%; H = 0.8%; N = 10.1%. Calc. for $C_6H_2Br_2N_2O$ (MW 277.9): C = 25.9%; H = 0.7%; N = 10.1% Br = 57.5%; O = 5.8%.

The spectrum obtained for the product from a mass spectrograph had a parent peak at $m/e$ 276 with the fragmentation pattern to be expected with two bromines present.

EXAMPLE 2

Biological testing of 4,6-dibromo-5-hydroxy-2-pyridine nitrile

A. Post-emergent herbicide evaluation.
Procedure:

Pots are filled with a sandy soil, and plants of any species considered appropriate (such as pigweed, field bindweed, velvet leaf, cotton, barnyard grass, foxtail, wild oat, and crabgrass) are grown to an average height of 2 to 4 inches. Plants are then sprayed to run-off with an aqueous solution or dispersion containing the test chemical at the desired concentration. The plants are maintained in the greenhouse and are sub-irrigated as necessary. Final readings are made 2 weeks after treatment. Readings represent the percent kill or control of growth on the treated plants when compared to untreated plants, with 0 = no visible effects and 100 = all plants dead. Compounds found active are subsequently tested over a range of rates which are less than the initial rate. The procedure is the same as described above except that additional species (such as soybean, corn, wheat, ragweed, Johnson grass, etc.) are used. Additionally, test chemicals may be applied to the soil surface by drenching or as a solid to preclude contact with foliage. If foliage is sprayed, the pots are subsequently maintained by sub-irrigation; if chemical application is made to the soil, the pots are top-watered.

Results:

TABLE I

Post-Emergent Herbicide Test Results for
4,6-dibromo-5-hydroxy-2-pyridine nitrile

| Plant Species | Concentration | Percent Control |
|---|---|---|
| Pigweeds | 1000 ppm | 100 |
| Soybeans | 4000 | 0 |
| Cotton | 4000 | 100 |
| German Millet | 4000 | 85 |
| White Winter Wheat | 2000 | 0 |
| Crabgrass | 4000 | 100 |
| Corn | 4000 | 0 |
| Sorghum/Milo | 4000 | 0 |
| Barnyard Grass | 4000 | 75 |
| Beans | 4000 | 70 |
| Wild Oats | 4000 | 65 |
| Yellow Foxtail | 4000 | 70 |
| Rape | 1000 | 100 |
| Cultured Rice | 4000 | 0 |
| Velvet Leaf | 2000 | 100 |
|  | 1000 | 85 |
| Morning Glory | 2000 | 100 |

B. Pre-emergent herbicide evaluation.

Procedure:

Pots are filled to within 1 inch of the top with a medium-textured soil and seeds of any species considered appropriate (such as pigweed, field bindweed, velvet leaf, cotton, barnyard grass, foxtail, wild oat and crabgrass) are sown in their appropriate area. The seeds are then covered with a ½ inch layer of a sandy soil and test chemicals formulated at the desired concentration are drenched onto the soil surface in sufficient volume to wet the top 1½ to 2 inches of soil. The pots are maintained in the greenhouse and are top-watered as necessary. Final readings are made about 2 weeks after treatment, the exact time depending upon the rate of plant growth. Readings are based on the germination and the growth of treated plants compared with that of untreated plants. Readings of 0% = no visible effects and 100% = all plants dead.

Evaluation:

Compounds found active are subsequently tested over a range of rates which are less than the initial rate. The procedure is the same as described above with the exceptions that the seeds of appropriate species (such as soybean, corn, wheat, ragweed, Johnson grass, etc.) are covered with the same medium-textured soil used to fill the pot, and the chemicals are sprayed onto the soil surface at the desired rate in sufficient volume to cover and wet the soil surface. The pots are maintained, top-watered, and graded as described above.

Results:

TABLE II

Pre-emergent Herbicide Test Results for
4,6-dibromo-5-hydroxy-2-pyridine nitrile

| Plant Species | Application Rate Lbs/Acre | % Control |
|---|---|---|
| Pigweeds | 2 | 100 |
| Soybean | 4 | 0 |
| Cotton | 4 | 0 |
|  | 10 | 100 |
| German Millet | 2 | 40 |
| White Winter Wheat | 4 | 0 |
| Crabgrass | 10 | 50 |
| Corn | 4 | 20 |
| Bindweed | 10 | 25 |
| Sorghum/Milo | 4 | 15 |
|  | 2 | 0 |
| Johnson Grass | 4 | 0 |
| Barnyard Grass | 10 | 40 |
| Beans | 10 | 60 |
| Wild Oats | 10 | 85 |
|  | 4 | 70 |
| Yellow Foxtail | 10 | 80 |
| Rape | 4 | 25 |
| Cultured Rice | 4 | 15 |
|  | 2 | 0 |
| Velvet Leaf | 10 | 40 |
| Morning Glory | 4 | 15 |

C. Comparison with BROMINIL as post-emergent herbicide.

Procedure:

All plants were grown in a greenhouse and sprayed with the test solution when they attained 1 to 2 inches in height. The test solutions were made up in water, using a 0.2% Tween 20 surfactant (polyoxyethylene derivative of a fatty acid partial ester of sorbitol) and were applied in a total spray volume equivalent to 300 gallons per acre.

Compound

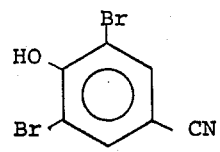 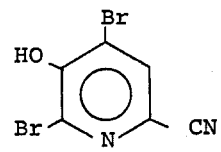

| Plant Species | Concentration Required for adequate control | |
|---|---|---|
| Wheat | 4000¹ ppm | 2000¹ ppm |
| Wild Oats | >4000 | 500 |
| Wild Mustard | 16 | 62 |
| Buckwheat | 16 | 250 |
| Morning Glory | 16 | 1000 |
| Bindweed | 500 | 4000 |

Note:
¹Minimum required for injury of wheat.

Discussion:

It will be seen from preceding Examples 2(A) and 2(B) that 4,6-dibromo-5-hydroxy-2-pyridine nitrile is a moderately active herbicide against weeds but shows low or nil activity against most crop plants at concentrations effective for weed control.

It is apparent from Example 2(C) that the pyridine compound of the present invention is generally less active than BROMINIL but, surprisingly, is 8 times more active against wild oats.

EXAMPLE 3

In standard tests of types conventionally employed for screening biologically active compounds, 4,6-dibromo-5-hydroxy-2-pyridine nitrile gave 100% control of two-spotted spider mites at a concentration of 400 parts per million and inhibited growth of the microorganism, Staphylococcus aureus, at 500 ppm.

We claim:

1. A compound of the formula

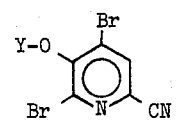

wherein Y is H or a cation of lithium, sodium, potassium, calcium, magnesium, barium, aluminum, a metal of atomic number 24 through 30, or tin.

2. The compound of claim 1 in which Y is H or $Na^+$.

3. The compound of claim 2 which is 4,6-dibromo-5-hydroxy-2-pyridine nitrile.

* * * * *

UNITED STATES PATENT OFFICE
CERTIFICATE OF CORRECTION

PATENT NO. : 3,956,338
DATED : May 11, 1976
INVENTOR(S) : Alin H. Gulbenk; Sven H. Ruetman.

It is certified that error appears in the above-identified patent and that said Letters Patent are hereby corrected as shown below:

Column 1, line 6: Serial No. incorrect; should be 541,812;

Column 5, line 56: Should be a comma after "fertilizers";

Column 5, line 60: "Preparations" spelled incorrectly;

Column 5, line 65: "thionyl" spelled incorrectly.

Signed and Sealed this

Twenty-eighth Day of September 1976

[SEAL]

Attest:

RUTH C. MASON
*Attesting Officer*

C. MARSHALL DANN
*Commissioner of Patents and Trademarks*